United States Patent
Hess et al.

(10) Patent No.: US 6,734,893 B1
(45) Date of Patent: May 11, 2004

(54) ENDOSCOPY ILLUMINATION SYSTEM FOR STROBOSCOPY

(75) Inventors: Markus Maria Hess, Berlin (DE); Michael Ludwigs, Berlin (DE)

(73) Assignee: Olympus Winter & IBE GmbH, Hamburg (DE)

( * ) Notice: Subject to any disclaimer, the term of this patent is extended or adjusted under 35 U.S.C. 154(b) by 0 days.

(21) Appl. No.: 09/205,217

(22) Filed: Dec. 4, 1998

(51) Int. Cl.[7] .............................. A61B 1/06; A61B 1/04
(52) U.S. Cl. .............................. 348/68; 348/65; 348/69
(58) Field of Search .............................. 600/179, 101, 600/109, 310, 586; 348/68, 69, 65; 362/1; 356/35.5

(56) References Cited

U.S. PATENT DOCUMENTS

| | | | | |
|---|---|---|---|---|
| 4,232,685 A | * | 11/1980 | Nagashima et al. | 600/586 |
| 5,020,904 A | * | 6/1991 | McMahan, Jr. | 356/35.5 |
| 5,585,840 A | * | 12/1996 | Watanabe et al. | 348/68 |
| 5,865,167 A | * | 2/1999 | Godik | 600/310 |

* cited by examiner

Primary Examiner—Chris Kelley
Assistant Examiner—Allen Wong
(74) Attorney, Agent, or Firm—Rankin, Hill, Porter & Clark LLP

(57) ABSTRACT

An endoscopy illumination system with a light-emitting element placed at the tip of an endoscope is disclosed. Pulses of light illuminate moving parts of the human body, enabling an observer to obtain information about the dynamical behavior of intracorporal structures, including vocal fold oscillations. An electronic control unit, which may obtain frequency and phase information from a microphone detecting the sound of an examinee's voice, generates light pulses for stroboscopy. The light-emitting elements are overmodulated light emitting diodes in the preferred embodiment. The endoscopy illumination system may be powered by batteries, rechargeables, or transformers. When image capture devices, including CCD and CMOS cameras, are used to record video images, electronic gating circuits activate the light-emitting elements, resulting in improved imaging.

10 Claims, 2 Drawing Sheets

1 LED
2 rigid endoscope
3 optical lens
4 wire to electronic control unit
5 silicone embedding wires

ENDOSCOPY ILLUMINATION SYSTEM FOR STROBOSCOPY

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

The present invention relates to endoscopy, and in particular to an endoscopy illumination system wherein (i) illumination is based on (stroboscopic) light pulses using at least one light-emitting element (e.g., a light emitting diode—LED) to obtain illumination of intracorporal structures, including the vocal folds, and where (ii) the light-emitting elements are powered and controlled by an electronic control unit within the endoscopy illumination system comprising features to obtain stroboscopic imaging.

In order to provide background information so that the invention may be completely understood and appreciated in its proper context, a short paragraph is given to acknowledge important inventions in the history of endoscopy of the larynx, and particularly stroboscopy, and reference is made to a number of prior art publications and patents.

Historically, the visualization of the inner parts of the body is referred to as endoscopy. Laryngoscopy specifically refers to the visualization of the larynx, which contains the sound producing vocal folds (also called vocal cords). Visualization of the larynx was first described by Garcia in the middle of the $19^{th}$ century when he used a mirror placed in the pharynx to observe vocal fold motion. For the past hundred years, the use of mirrors has been considered routine for laryngologists. The rapid vibrations of the vocal folds cannot be detected using continuously emitting light sources, because typical frequencies for voice production ranging from 70 Hz up to 400 Hz are too fast for our eyes to see. The technique of stroboscopy allows the physician a clear view of the vocal folds, even when they are vibrating rapidly. In 1878, Oertel used a device to visualize the rapid vocal fold motions during sound production (phonation) through the use of stroboscopy techniques. Since then, three major image routing techniques were—and currently still are—used clinically to help visualize the vocal fold motions via stroboscopy: (a) indirect observation with a mirror held into the pharynx of the examinee and illumination provided by an external light source, (b) intrapharyngeal placement of a rigid endoscope (also called a telescope) through the mouth (transorally), whereby the telescope contains an optical apparatus with lenses and mirrors as well as light conductors for illumination of the pharynx and larynx, and (c) the use of a fiberscope, with its far end also placed within the pharynx, but routed through the nasal cavity (transnasally), wereby the fiberscope contains an optical compartment for image transmission as well as glass fiber light conductors for illumination. In all three techniques, illuminating light is provided through extracorporal light sources.

For non-moving anatomical structures, color images are preferred clinically because they contain more information than monochrome images. For the examination of dynamic features, e.g., the vibration patterns of the vocal folds using stroboscopy, monochrome images with high gray scale resolution are considered sufficient. Numerous publications considering dynamic behavior of the vibrating vocal folds are based on black and white imaging. A historical overview of stroboscopy from the perspective of a clinician is given in an article by J. Wendler (Stroboscopy. Journal of Voice, Vol.6 No.2, pp 149–154, 1992, Raven Press, N.Y.). Although the technique of stroboscopy has been known and used for more than a hundred years, stroboscopy systems still are heavy, large, and expensive to build.

Because LEDs are used for illumiination in the preferred embodiment of this invention, some features may be pointed out in advance. Energy supplying elements, such as batteries, are capable of powering an electronic circuit as well as an illumination source, e.g. LEDs. LEDs are also a quite cheap light source (a red LED with very bright light emission presently costs about 0.80 US$). Light intensity is mainly dependent on current flow, and usually an upper current threshold—for continous light emission purposes—is typically at 20 Milliamperes (mA). More precisely, a continuous current of 20 mA will not destroy the LED. Continuously applied higher currents, say, 50 mA or 60 mA, may lead to higher light energy output, but also to a reduced life span of minutes, or seconds. To give an example of a possible limitation, we tried to find out where a maximum may be reached for a specific LED type. In so-called ultra bright red LEDs, the life span was less than five minutes when 60 mA were continuously applied. However, pulsed loading of the LEDs with much higher currents is well tolerated.

German Pat. No. DE 3,432,018 to Nagasaki et al., U.S. Pat. No. 4,816,909 to Kimura et al., U.S. Pat. No. 5,363,135 to Inglese disclose the use of light emitting diodes arranged in the tip part of the insertable part of an endoscope to provide illumination for imaging, more specifically, to adjust for image sensor device—specific conditions and requirements, such as adjustment for pixel numbers, spectral characteristics, and image colour separation. However, the above mentioned inventions do not teach and cannot be applied to obtain stroboscopy illumination, because no triggering parts including a frequency detecting device (e.g., for the human voice) are incorporated. Furthermore, the above mentioned inventions do not provide means for matching single pulses of light with individual frames in a camera system. Stroboscopy features prominent in the present invention are therefore not anticipated in the abovementioned patents.

Whatever the precise merits, features and advantages of the above cited references and prior art, none of them achieves or fulfills the purposes of the present invention. A principal object of the present invention is a system for stroboscopic endoscopy that is small, light weight, and inexpensive to build. The prior art devices fail to be satisfactory, because they do not utilize the advantages of pocket-sized electronics, are not power outlet independent, are not portable for hand-held examinations, are not cheap to build, and do not provide to match light pulses to the active frame intervals of image recording systems, as is all provided in the present invention. Customly available light sources for clinical rigid and flexible stroboscopy are heavy (they weigh more than 5 kg), they are all power outlet dependent, and they are mostly based on xenon or halogen light emitting bulbs with far more than one hundred Watts of energy consumption, leading to heat emission undesireable for endoscopy, and cost at least 5,000 US$. The main prerequisites for future clinical needs of small sized, light-weight, and inexpensive stroboscopy devices (Wendler, 1992) are still not met.

It is another principal object of the present invention to provide an electronic control unit within the endoscopy illumination system with characteristics that will enable achievement of sufficient illumination of the objects inside the body. Among the features necessary for stroboscopy are short light pulses with high intensities, rapid increase and more rapid decay than xenon light bulb flashes, machine-set fixed and/or externally triggered flashing capabilities from lower than 100 Hz up to more than 400 Hz. All above mentioned features are realized in the present invention.

It should be noted that use of inexpensive, detachable light-emitting elements, such as LEDs for diagnostic procedures, may have the additional potential of being used only once. Single-use light-emitting elements could reduce costs by avoiding the need for special sterilization procedures.

Another object is to provide a device that can be disassembled quickly and easily for transportation to an examination site, such as in a bedside patient examination procedure, or quick follow-up examination outside the office site, and that allows for more practical screening of a large population. The availability of an inexpensive and versatile stroboscopic endoscope could have a positive impact on the health of many people in developing countries.

To avoid double exposures, it is important that the illumination source flash only once per video frame. The electronic control unit of the present invention may be designed to ensure that only one flash accompanies a single image acquisition, thus avoiding double exposures and the resulting blurred images during stroboscopy recordings.

The abovementioned features can all be realized, when our endoscopy illumination system is used in combination with ultra bright LEDs within its light-emitting element.

BRIEF SUMMARY OF THE INVENTION

The principal object of the present invention is to provide an endoscopy illumination system comprising light-emitting elements such as light emitting diodes, driven by an electronic control unit. The system should be light-weight, easily portable, pocket-sized, power outlet independent, easy to handle, and inexpensive, while also providing sufficient illumination for stroboscopy purposes. Pulsed light from said light-emitting element, powered and controlled by said electronic control unit, provides adequate light pulse emissions for direct visual examination, as well as adequate illumination, when image processing devices, including solid state cameras, CCD and CMOS, and image recording systems are attached.

BRIEF DESCRIPTION OF THE SEVERAL VIEWS OF THE DRAWING

The following figures will illustrate a preferred embodiment of the present invention.

DETAILED DESCRIPTION OF THE INVENTION

Figure 1:
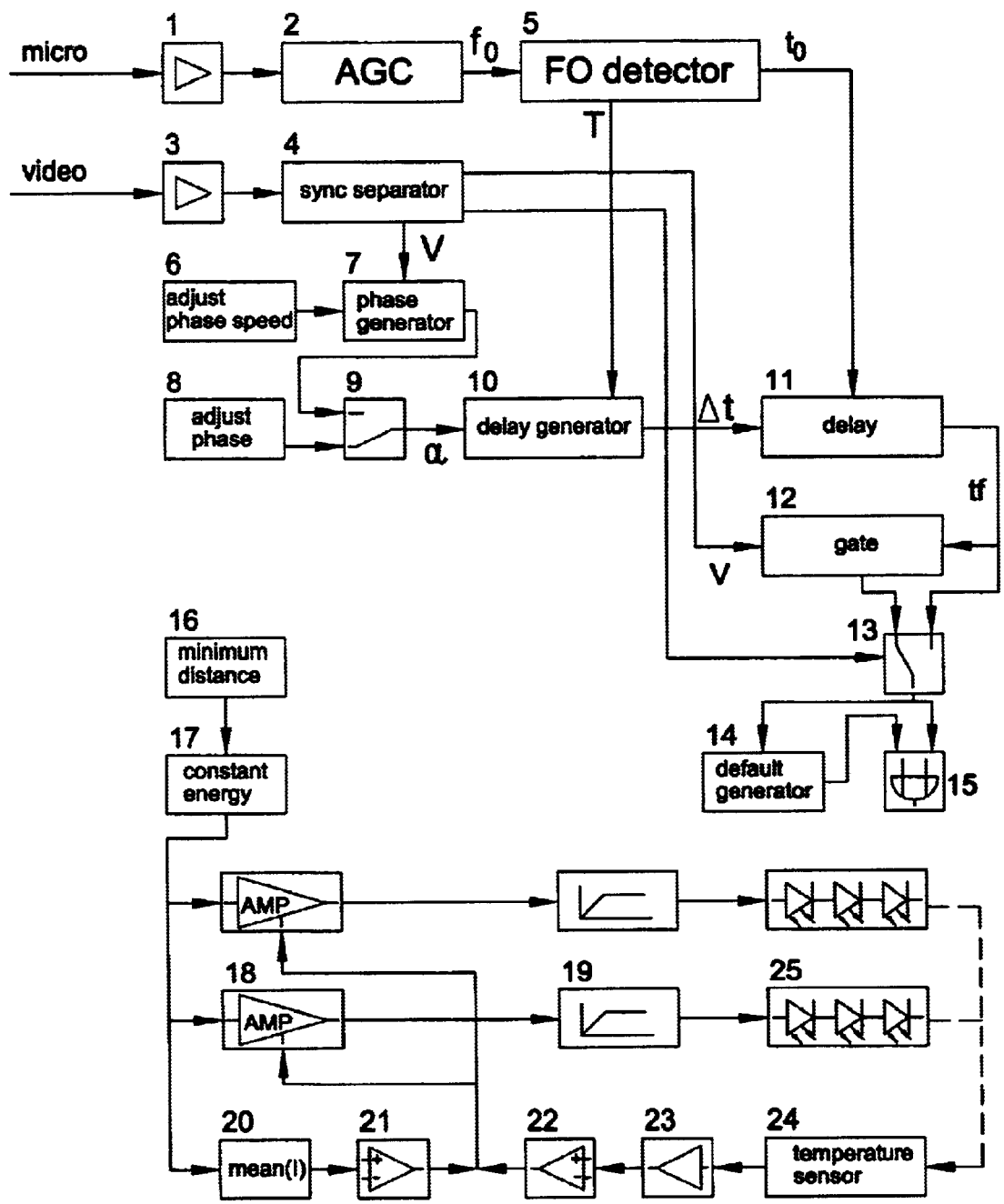
FIG. 1 is a schematic diagram of the endoscopy illumination system.

Refer now to FIG. 1, which is an overall schematic drawing of a preferred embodiment of the invention. We will first describe the electronic control unit with its different components, followed by a description of the light-emitting element.

a) Electronic Control Unit

Within the electronic control unit, two input signals are processed: a microphone signal and a video signal from the image capture device. During stroboscopy, voicing of an examinee leads to an acoustic output which is recorded with a microphone. The microphone signal is amplified by a high impedance amplifier (1) for use with crystal or electret microphones. The output signal is routed to an automatic gain control (AGC) module (2). This module reduces both rapid and slow fluctuations of amplitude (normalization of shimmer). By the use of different time constants for the initial signal onset (high and rapid response for amplification) and for the stable phase of phonation (lower and slower response for amplification) a signal of nearly constant amplitude is obtained, as is required for satisfactory stroboscopy triggering. The F0-detector (5) receives the signal from the AGC module (2), separates the fundamental frequency, and generates a signal T, where the amplitude is proportional to the period of the fundamental frequency. T is fed into the delay generator (10), which will be described later. The F0-detector (5) also generates a pulse train signal to in synchrony and phase-locked with the incoming microphone signal (accordingly, t0 is a voice-related, triggered, pulsed output signal). The signal to is fed into the delay module (11). This delay module delays each incoming pulse of t0 by $\Delta t$, which is the time delay for an angle alpha for a given frequency F0 (signaled from the delay generator (10)) and produces an output signal tf. The pulses of tf appear each time when F0 passes alpha ($\alpha$). This signal tf now has the required firing pattern for stroboscopy. Special requirements have to be followed when video imaging is used, as we now explain.

The video signal from an image capture system, e.g., a CCD camera, is routed through an impedance converter (3) and fed into a synchronisation signal separator (4). The synchronisation separator (4), which may be programed for NTSC and PAL signals, has three output signals. First, a vertical synchronisation signal V is generated. The V signal is routed to the phase generator (7), which itself produces a periodically changing signal $\alpha$ representing the actual phase for the slow motion image presentation. The phase generator (7) is synchronised with the vertical synchronisation signal V. The phase is incremented constantly with each video half frame. The increment and period time for one complete strobe-cycle oscillation of the vocal folds (which is usually displayed at about 1 cycle per second) is controled by a speed adjustment module (6). If a 'motionless', phase-synchronous image is desired, a signal from the adjustment module (8) is generated and routed through the switch (9). Thus, by selection of switch setting (9), the user can decide whether slow motion imaging (provided via input (7)) or a motionless, 'freeze'-like image mode (provided via input from (8)) is activated. The delay generator (10) feeds its output signal $\Delta t$ ($\Delta t = T \cdot \alpha / 360°$) into the abovementioned delay module (11). $\Delta t$ is proportional to T, which enables a frequency independent visualization of similar vocal fold oscillation phases.

The synchronisation separator (4) also puts out two other signals: one signal is directed to the gate module (12), the other to a mode switch (13). The mode switch (13) allows for manual selection of the modes EYE, CAM or AUTO. In the EYE mode, every pulse from tf is used. In the CAM mode, only the pulses selected by the gate module (12) are used. In the AUTO mode, the CAM mode is automatically selected when a video signal is present, which is sensed by the incoming signal from the synchronisation separator (4). This mode switch is integrated to provide stroboscopy without video recording, e.g., in a bedside examination setting.

The gate module (12) regulates and limits light exposure for video frames. For an equal exposure, a constant number of light pulses (flashes) is gated for each frame. To avoid the effect of multiple exposure with different vocal fold positions, each light pulse within the same frame must be generated at the same angle alpha. In the case of slow motion visualization of the vocal fold movements, the value of alpha is held constant for each frame. This requirement is provided by the phase generator (7). The number of pulses depend on the frequency of the video signal and the fundamental frequency of the microphone signal. The gating module receives signals from the synchronisation separator (4) and the delay module (11). The synchronisation input signal defines the (programable) active image acquisition period (active interval) of the CCD chip. This information is fed into the gating module (12), which is set to permit only a constant number of pulses to pass in the active interval of the CCD. All additional pulses within the same frame will be rejected from passing through to the gate module (12). The gate module (12) signal does not trigger the LEDs to flash, it rather permits or rejects voltage pulses within desirable time windows (within the active interval) to pass through. For the next active interval, signaled by a new incoming start-signal from the synchronisation separator (4), the abovementioned process starts again.

In the case that no stroboscopy signals are produced and no pulsed signals are routed through the mode switch (13), a default generator (14) generates frequent pulses to provide illumination. The default generator (14) is started whenever the time between the incoming strobe pulses from tf exceeds a (programable) time limit. The frequency is set according to the input requirements of the particular LEDs used (to guarantee their maximal life span). The OR-gate (15) integrates this default feature.

The modules shown at the bottom of FIG. 1 (16–25) regulate energy consumption, current limits, duty cycle duration, and temperature thresholds for the LEDs, and adapt the stroboscopically required light pulses of the electronic control unit to the particular LEDs employed.

The minimum distance module (16) eliminates pulses whenever the frequency of the strobe pulses are very high (e.g., higher than 500/sec) and, therefore, minimal time intervals occur (frequency limiter). This preserves the life span of the LEDs. The pulse-duration is controlled by the constant energy module (17) to reach a constant illumination exposure of the video frames and to constantly regulate the power consumption of the LEDs. The duration of a duty-cycle duration depends on the frequency F0, but should not exceed 1 millisecond to avoid blurring of moving elements within an image. A programable power factor is used for matching the requirements of the LED types utilized. To reduce the supply voltage, a variable number of parallel current amplifiers (18) may be used. In the preferred embodiment, 4 LEDs are powered by 2 current amplifiers (18). Current limiters (19) are added to limit the current to a threshold above which additional current will not result in further light output. The setting of the current limiters depends on the type of LEDs used. The temperature of the LEDs (25) is registered with a temperature sensor (24), e.g., a thermistor, for safety reasons. Its output is amplified (23) and activates the comparator (22) in case of LED overheating, resulting in negative feedback to the amplifier (18). Another circuit concerned with safety utilizes a mean current comparator (20), which detects critical power output over time and limits the current flow in the current amplifiers (18).

b) Light-emitting Element

Figure 2:
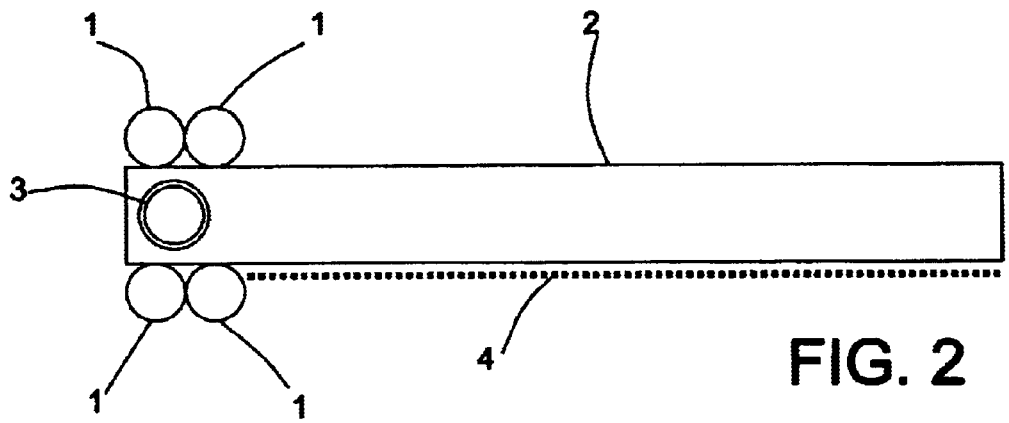
FIG. 2 is a bottom view of the light-emitting element specifying the LED positions at the tip of a rigid endoscope in this preferred embodiment.
Figure 3:
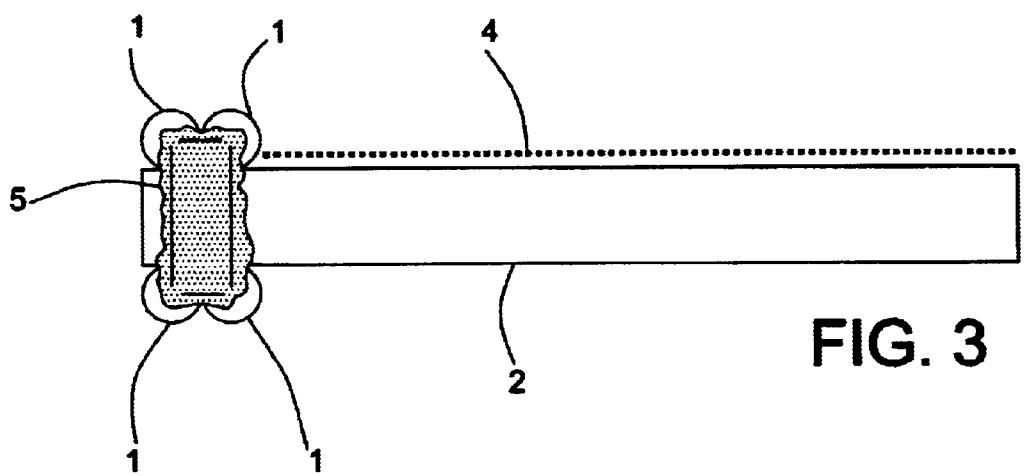
FIG. 3 is a top view of the light-emitting element showing the silicone embedding connecting wires of the LEDs.
Figure 4:
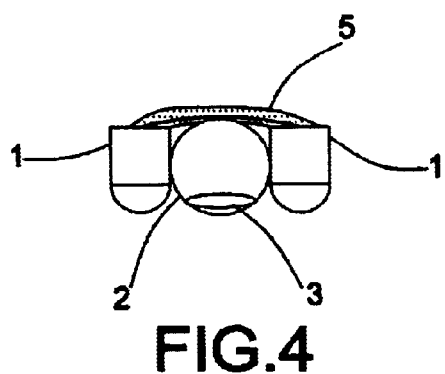
FIG. 4 is a frontal view of the light-emitting element with lateral LED positions at the tip of a rigid endoscope.

Refer now to FIGS. 2, 3, and 4, which show a preferred embodiment of the light-emitting element. This light-emitting element has four LEDs (reference number 1 in FIGS. 2–4). It may be attached to the tip of a rigid endoscope (reference number 2 in FIGS. 2–4). The two power-supplying wires (reference number 4 in FIGS. 2 and 3) are routed next to the endoscope along its shaft and are connected to the electronic control unit (to the current limiters (reference number 19 in FIG. 1)). The wires of the LEDs and their connection to the wires routed to the electronic control unit are covered by silicone (reference number 5 in FIGS. 3 and 4), which serves four purposes: 1) electrical isolation of the wires going into the LED casing; 2) facilitation for cleaning in soluble detergents; 3) enhancement of wire stability; and 4) smoothing of the surfaces of the insertable light-emitting element in laryngoscopy settings.

The electronic control unit and the light-emitting element are powered by one or two 9 Volt batteries, depending on the voltage needed. A manual power switch allows for voltage selection (9V/18V).

With this preferred embodiment, we present an easily portable, pocket-sized, lightweight, power outlet independent, easy to handle, inexpensive endoscopy illumination system. The system allows a direct view of vibrating structures, using an acoustic signal to synchronize light pulses with vibrations. It also provides single-flash-per-frame pulsed light emissions when a CCD camera is attached. Thus, the preferred embodiment of the present invention has fulfilled the objects stated at the outset.

The foregoing description of the preferred embodiment of the invention has been presented for the purpose of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. An endoscopy illumination system for supplying an illumination light for endoscopy purposes with a light-emitting element and an electronic control unit comprising:
   (a) a light-emitting element, being detachable, connected to said electronic control unit and detachably attached to the tip of an elongated part insertable into a human body comprising an endoscope, a tip-mounted CCD or CMOS camera, said light-emitting element being directed to the object of examination, said light-emitting element comprising light emitting diodes over-modulatable in a pulsed mode, and said pulses comprising frequency-associated pulses for stroboscopy use;
   (b) an electronic control unit comprising:
      (ba) a movement-detection circuit for detecting a movement of an object of examination from signals supplied from an external source comprising microphone-related signals or electroglottography-related signals, said movement detection circuit being attached to or integrated within said electronic control unit, where said movement-related signals are further processed;

(bb) a delay circuit integrated within said electronic control unit, delaying pulses in a pulsed trigger signal with a controlable phase delay from 0° to 360° in relation to the movements of the object of examination, said delayed pulse trigger signal directly or indirectly activating said light-emitting element, comprising pulsed flashing modes for stroboscopy, for example to illuminate for 'motionless' phase-locked or 'slow-motion' imaging C.

2. An endoscopy illumination system according to claim 1 wherein said electronic control unit comprises a gating circuit integrated within said electronic control unit gating said delayed pulsed trigger signals from said delay circuit according to an input signal received from a detachably connected image capture device, whereby pulsed signals from said delay circuit are gated for pulses within desired active image acquisition phases of said image capture device, and where the gating circuit output signal activates said light-emitting element, resulting in improved imaging, including prevention of interference patterns on an image display device and avoiding streak formation on an image screen.

3. An endoscopy illumination system according to claim 2 wherein said pulsed signals from said delay circuit are gated for pulses within desired active image acquisition phases of said image capture device, and where a constant illumination of image frames is provided by the number of illuminating flashes.

4. An endoscopy illumination system according to any of claims 1, 2, or 3 wherein said electronic control unit comprises a gating circuit integrated within said electronic control unit gating said delayed pulsed trigger signals from said delay circuit according to an input signal received from a detachably connected image capture device, whereby pulsed signals from said delay circuit may lead to more than one illuminating flashes within one image frame, but only when similar oscillation phases are present, i.e., the oscillating object may only be illuminated at the same position.

5. An endoscopy illumination system according to claim 1, wherein said electronic control unit comprises an automatically activated electrical default generator circuit integrated within said electronic control unit generating a signal to provide illumination within time intervals where no triggering signal is present.

6. An endoscopy illumination system according to claim 1, wherein said electronic control unit comprises an automatically activated switch integrated within said electronic control unit enabling pulse triggered illumination or default generator circuit illumination in the case no image capture device is attached or integrated to the electronic control unit.

7. An endoscopy illumination system according to claim 1, wherein said electronic control unit comprises a circuit integrated within said electronic control unit to overmodulate said LEDs in said light-emitting element, providing and controlling maximum energy output for duty cycles and also providing and controlling mean energy consumption over time, including means for improving safety and reliability such as low pass filtering, light-emitting element temperature control, current limiting, and voltage limiting.

8. An endoscopy illumination system according to claim 1, wherein said endoscopy illumination system includes intracorporal and/or extracorporal light emitting element positions, where extracorporal light is routed by means of a conductor into the body, comprising extracorporal light emitting diode(s) connected to at least one glass fiber cable.

9. An endoscopy illumination system according to claim 1, wherein said endoscopy illumination system utilizes related semiconductor elements such as laser diodes and light emitting diodes with invisible light.

10. An endoscopy illumination system according to claim 1, wherein said endoscopy illumination system utilizes either power-outlet-dependent and/or power-outlet-independent energy supplying elements including, but not limited to: batteries, rechargeables, and transformers.

* * * * *